US011116929B2

(12) United States Patent
Giudice et al.

(10) Patent No.: US 11,116,929 B2
(45) Date of Patent: Sep. 14, 2021

(54) PEDIATRIC CPAP MASK

(71) Applicant: 3B Medical, Inc., Winter Haven, FL (US)

(72) Inventors: Angela Giudice, Kissimmee, FL (US); Adam Joshua Mills, Auburndale, FL (US); Albert A. Lucio, Haines City, FL (US)

(73) Assignee: 3B MEDICAL, INC., Winter Haven, FL (US)

( * ) Notice: Subject to any disclaimer, the term of this patent is extended or adjusted under 35 U.S.C. 154(b) by 190 days.

(21) Appl. No.: 15/917,985

(22) Filed: Mar. 12, 2018

(65) Prior Publication Data

US 2019/0275279 A1    Sep. 12, 2019

(51) Int. Cl.
| A61M 16/06 | (2006.01) |
| A61M 16/08 | (2006.01) |
| B29C 45/00 | (2006.01) |
| B29L 31/00 | (2006.01) |
| B29K 105/00 | (2006.01) |
| B29K 83/00 | (2006.01) |

(52) U.S. Cl.
CPC .... A61M 16/0688 (2014.02); A61M 16/0875 (2013.01); B29C 45/0053 (2013.01); *A61M 2207/00* (2013.01); *A61M 2240/00* (2013.01); *B29K 2083/00* (2013.01); *B29K 2105/0061* (2013.01); *B29K 2105/0097* (2013.01); *B29L 2031/753* (2013.01)

(58) Field of Classification Search
CPC .......... A61M 16/0688; A61M 16/0694; A61M 16/0683; A61M 16/0497; A61M 16/0605; A61M 2025/022; A61M 16/0226; A61M 16/0057; A61M 16/0463; A61M 16/049; A61M 16/06; A61M 16/0616; A61M 16/0633; A61M 16/0816; A61M 16/0841; A61M 2205/0238; A61M 2205/59; A61M 2210/0618; A61M 2210/0625; A61M 2240/00
See application file for complete search history.

(56) References Cited

U.S. PATENT DOCUMENTS

| 3,020,260 | A | | 2/1962 | Nelson | |
| 3,556,097 | A | * | 1/1971 | Wallace | A61M 16/06 128/202.23 |
| 5,676,133 | A | * | 10/1997 | Hickle | A61M 16/00 128/202.27 |
| 6,196,223 | B1 | | 3/2001 | Belfer et al. | |

(Continued)

FOREIGN PATENT DOCUMENTS

| EP | 0300620 A1 | 1/1989 |
| EP | 0322118 A1 | 6/1989 |

(Continued)

*Primary Examiner* — Annette Dixon
(74) *Attorney, Agent, or Firm* — Carlson, Gaskey & Olds, P.C.

(57) ABSTRACT

A mask configured to deliver pressurized airflow according to an exemplary aspect of the present disclosure includes, among other things, a central portion configured to surround a nose of a patient, a first pair of wings projecting from opposite sides of the central portion, and a second pair of wings projecting from opposite sides of the central portion. The disclosed mask has particular benefits to pre-term infants. A system and method are also disclosed.

23 Claims, 3 Drawing Sheets

(56) References Cited

U.S. PATENT DOCUMENTS

| | | |
|---|---|---|
| 6,846,508 B1 | 1/2005 | Colas et al. |
| 7,077,138 B2 * | 7/2006 | Bateman ............ A61M 16/0463 128/206.14 |
| 2001/0029954 A1 * | 10/2001 | Palmer .............. A61M 16/0488 128/207.17 |
| 2003/0145859 A1 * | 8/2003 | Bohn .................... A61M 16/06 128/206.24 |
| 2006/0096598 A1 * | 5/2006 | Ho ........................ A61M 16/06 128/206.24 |
| 2007/0106016 A1 * | 5/2007 | Zhu ........................ A43B 13/04 524/588 |
| 2009/0223522 A1 * | 9/2009 | Hernandez ........ A61M 16/0605 128/206.26 |
| 2010/0000534 A1 * | 1/2010 | Kooij ................ A61M 16/0666 128/204.18 |
| 2010/0229872 A1 * | 9/2010 | Ho .................... A61M 16/0666 128/206.25 |
| 2015/0250970 A1 * | 9/2015 | Bowsher ........... A61M 16/0616 128/205.25 |
| 2017/0224942 A1 * | 8/2017 | Barbour ............ A61M 16/0672 |
| 2019/0240441 A1 * | 8/2019 | Dumas De La Roque ................ A61M 16/0057 |

FOREIGN PATENT DOCUMENTS

| | | |
|---|---|---|
| GB | 849885 | 9/1960 |
| GB | 945580 | 1/1964 |
| GB | 2192142 A | 1/1988 |

* cited by examiner

PEDIATRIC CPAP MASK

TECHNICAL FIELD

This disclosure relates to a pediatric CPAP mask, which incorporates adhesive to attach to a patient. The patient may be a pediatric patient, including a neonatal patient such as a pre-term infant. This disclosure also relates to systems and methods corresponding to the disclosed mask.

BACKGROUND

Unfortunately, it is quite common for neonatal patients, such as pre-term infants, to have some form of respiratory disorder. For these newborns, continuous positive airway pressure (CPAP) therapy systems may be beneficial, as CPAP provides a non-invasive respiratory support mechanism.

CPAP therapy systems increase air pressure in a patient's throat so that their airway does not collapse as they breathe. CPAP therapy systems consist of (1) a flow generator for creating the flow of air, (2) a conduit—typically a heated or insulated hose or other flexible connector—for carrying the air to the patient, and (3) an interface—such as a mask, together with equipment that secures it to the patient's head—for delivering the pressurized air to the patient's airway.

Traditionally, headgear has been required to secure the mask to a patient's head. The headgear typically attaches to the mask and wraps around a patient's head. However, most headgear on the market is too large for use with neonatal patients—in particular, pre-term infants. Further, headgear may be cumbersome and uncomfortable for such patients. Accordingly, there is a need for a CPAP mask appropriate for use with pre-term infants and other small pediatric patients.

SUMMARY

A mask configured to deliver pressurized airflow according to an exemplary aspect of the present disclosure includes, among other things, a central portion configured to surround a nose of a patient, a first pair of wings projecting from opposite sides of the central portion, and a second pair of wings projecting from opposite sides of the central portion.

In a further non-limiting embodiment of the foregoing mask, each wing of the first and second pairs of wings is at least partially provided by an adhesive material.

In a further non-limiting embodiment of any of the foregoing masks, the mask is formed entirely of silicone.

In a further non-limiting embodiment of any of the foregoing masks, a rim of the central portion is at least partially provided by the adhesive material.

In a further non-limiting embodiment of any of the foregoing masks, the adhesive material is integrally formed with the mask.

In a further non-limiting embodiment of any of the foregoing masks, the adhesive material is a two compound silicone elastomer.

In a further non-limiting embodiment of any of the foregoing masks, the first pair of wings each include an upper edge having a length greater than a length of a lower edge thereof.

In a further non-limiting embodiment of any of the foregoing masks, the second pair of wings each include an upper edge having a length less than a length of a lower edge thereof.

In a further non-limiting embodiment of any of the foregoing masks, a width of the mask between ends of the first pair of wings is less than a width of the mask between ends of the second pair of wings.

In a further non-limiting embodiment of any of the foregoing masks, the first pair of wings are above the second pair of wings.

In a further non-limiting embodiment of any of the foregoing masks, a ratio of the width of the mask between ends of the first pair of wings to the width of the mask between ends of the second pair of wings is between about 0.7 and 0.9.

In a further non-limiting embodiment of any of the foregoing masks, a ratio of a width of the central portion to a width of the mask between ends of the first pair of wings is between about 0.5 and 0.7.

In a further non-limiting embodiment of any of the foregoing masks, a ratio of the width of the central portion to a width of the mask between ends of the second pair of wings is between about 0.6 and 0.9.

In a further non-limiting embodiment of any of the foregoing masks, a ratio of a height of the second pair of wings to a height of the first pair of wings is between about 0.5 to 1.5.

In a further non-limiting embodiment of any of the foregoing masks, the ratio of the height of the second pair of wings to the height of the first pair of wings is between about 0.6 and 1.0.

In a further non-limiting embodiment of any of the foregoing masks, a ratio of the height of the first pair of wings to a height of the central portion is between about 0.1 and 0.5.

In a further non-limiting embodiment of any of the foregoing masks, a ratio of the height of the second pair of wings to a height of the central portion is between about 0.1 and 0.5.

In a further non-limiting embodiment of any of the foregoing masks, each of the first pair of wings projects along an axis oblique to a centerline of the mask, and each of the second pair of wings includes a lower edge curved following a radius having an origin on a centerline of the mask.

A system for delivering pressurized airflow according to an exemplary aspect of the present disclosure includes, among other things, a flow generator configured to output a pressurized airflow, a conduit, and a mask in fluid communication with the conduit. The mask includes a central portion configured to surround a nose of a patient, a first pair of wings projecting from opposite sides of the central portion, and a second pair of wings projecting from opposite sides of the central portion.

A method of manufacturing a mask according to an exemplary aspect of the present disclosure includes, among other things, injecting a soft elastomer compound into a mold to form an initial structure of the mask. The initial structure of the mask includes a central portion. The method further includes providing an adhesive gel on the surface of the initial structure. The adhesive gel is injected into the mold and is molded to the surface of the initial structure so as to at least partially form a first pair of wings projecting from the central portion and a second pair of wings projecting from the central portion. Each wing of the first and second pairs of wings is at least partially made of the adhesive gel.

DETAILED DESCRIPTION

This disclosure relates to a pediatric CPAP mask, which incorporates adhesive to attach to a patient. The patient may be a pediatric patient, including a neonatal patient such as a pre-term infant. This disclosure also relates to systems and methods corresponding to the disclosed mask.

The disclosed mask provides a reliable and easy-to-use interface for a CPAP therapy system. The mask is appropriate for use with neonatal patients such as pre-term infants. To attach the disclosed mask, the mask is oriented in an appropriate position on the patient's face, and then pressure is applied to the mask causing the adhesive to bond to the patient's face. The adhesive secures the mask to the patient's skin without the need for headgear. The mask retains an appropriate air seal even when the patient lies on his or her side. The mask may be relatively inexpensively made, making it suitable for one-time use applications. In some examples the mask may be reusable, while in other examples the mask is intended to be disposable. As will be appreciated, the mask is particularly useful in neonatal applications, in particular because it may be difficult to affix traditional mask headgear to infants.

Figure 1:
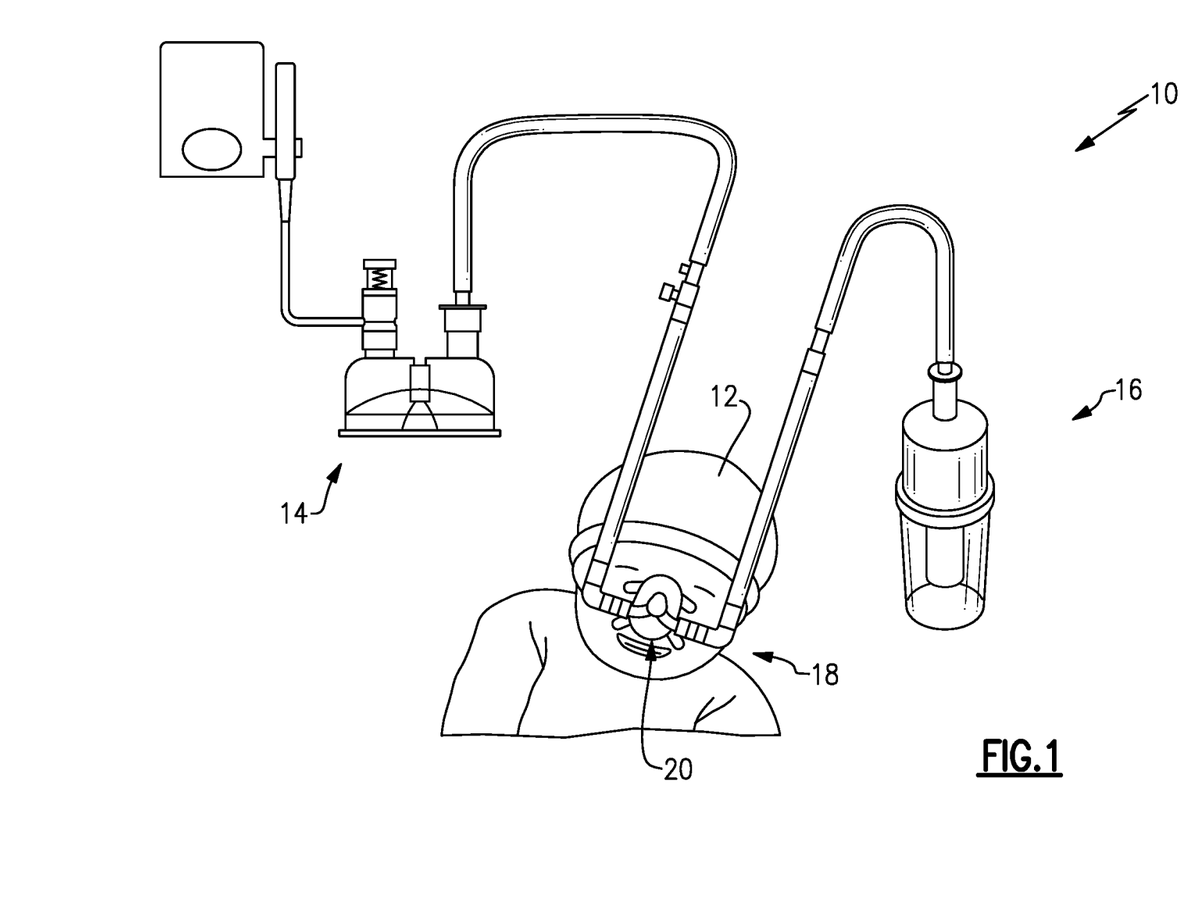
FIG. 1 illustrates an example CPAP system.

FIG. 1 illustrates an example CPAP system 10. As illustrated, the system 10 is a bubble CPAP system, which is commonly used for newborn patients. A newborn patient is illustrated at 12. The system 10 includes, among other things, a gas source 14, a pressure generator 16, and a patient interface 18. The patient interface 18, in this example, includes a mask 20 configured for placement over a patient's nose. The mask 20 is described in detail below. This disclosure is not limited to use with bubble CPAP systems, and applies to other types of CPAP systems. Further, while two conduits are attached to the mask 20 in FIG. 1, this disclosure also extends to systems with a mask connected to one conduit.

Figure 2:
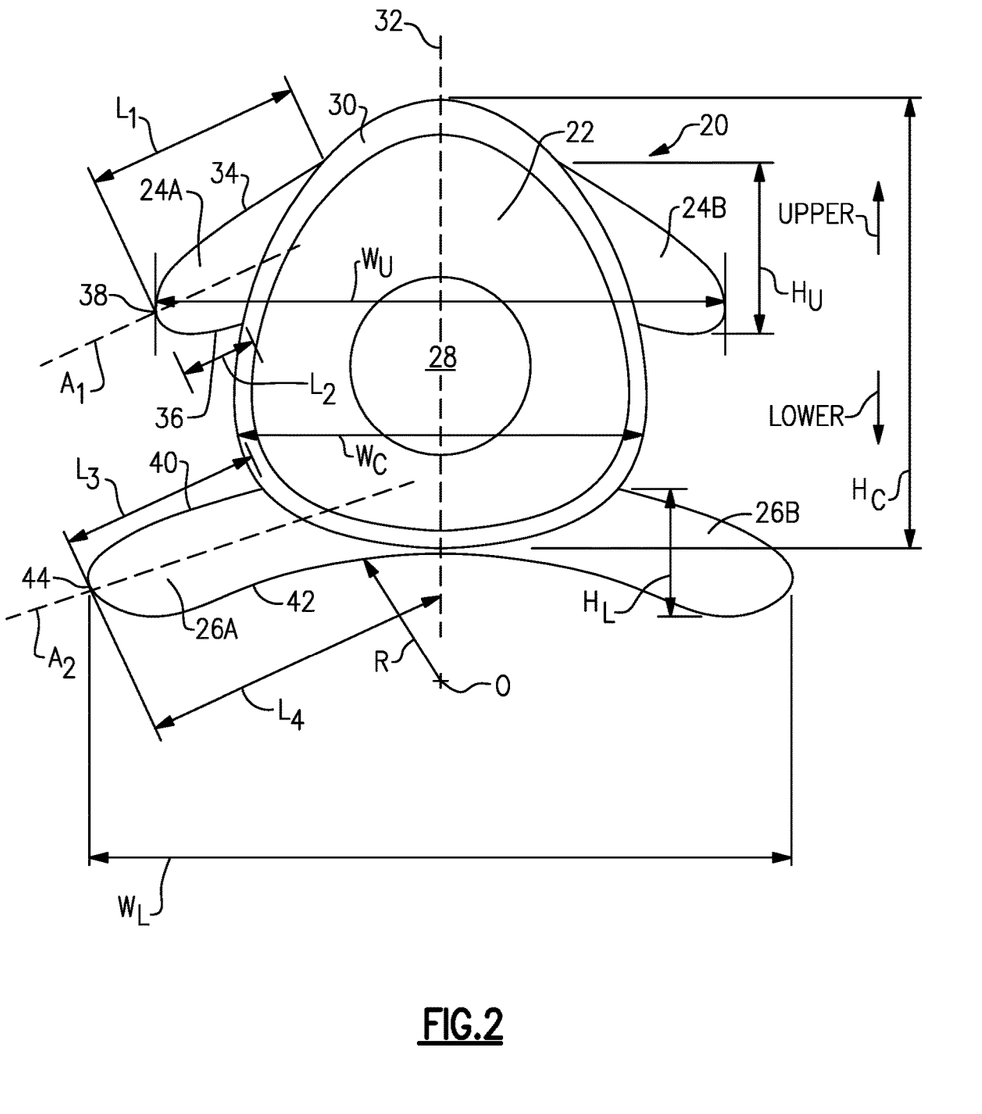
FIG. 2 is a front view of an example mask.

FIG. 2 illustrates an example mask 20. The mask 20 includes of a central portion 22 which is configured to surround a patient's nose. In this example, a top of the central portion 22 is configured to rest on the bridge of a patient's nose, and the bottom of the central portion 22 is configured to rest above a patient's upper lip.

The example mask 20 further includes two pairs of wings projecting from the central portion 22. A pair of upper wings 24A, 24B project from opposite sides of the central portion 22 and are configured to adhere to a patient's upper cheek proximate to the nose and just below the eyes. Further, a pair of lower wings 26A, 26B project from opposite sides of the central portion 22 and are configured to adhere to the area above a patient's upper lip. The terms "top," "bottom," "upper," and "lower" are used with reference to the orientation of the mask 20 in FIG. 2, and are used for purposes of explanation only. The "upper" and "lower" directions are labeled in FIG. 2 for avoidance of doubt.

Figure 3:
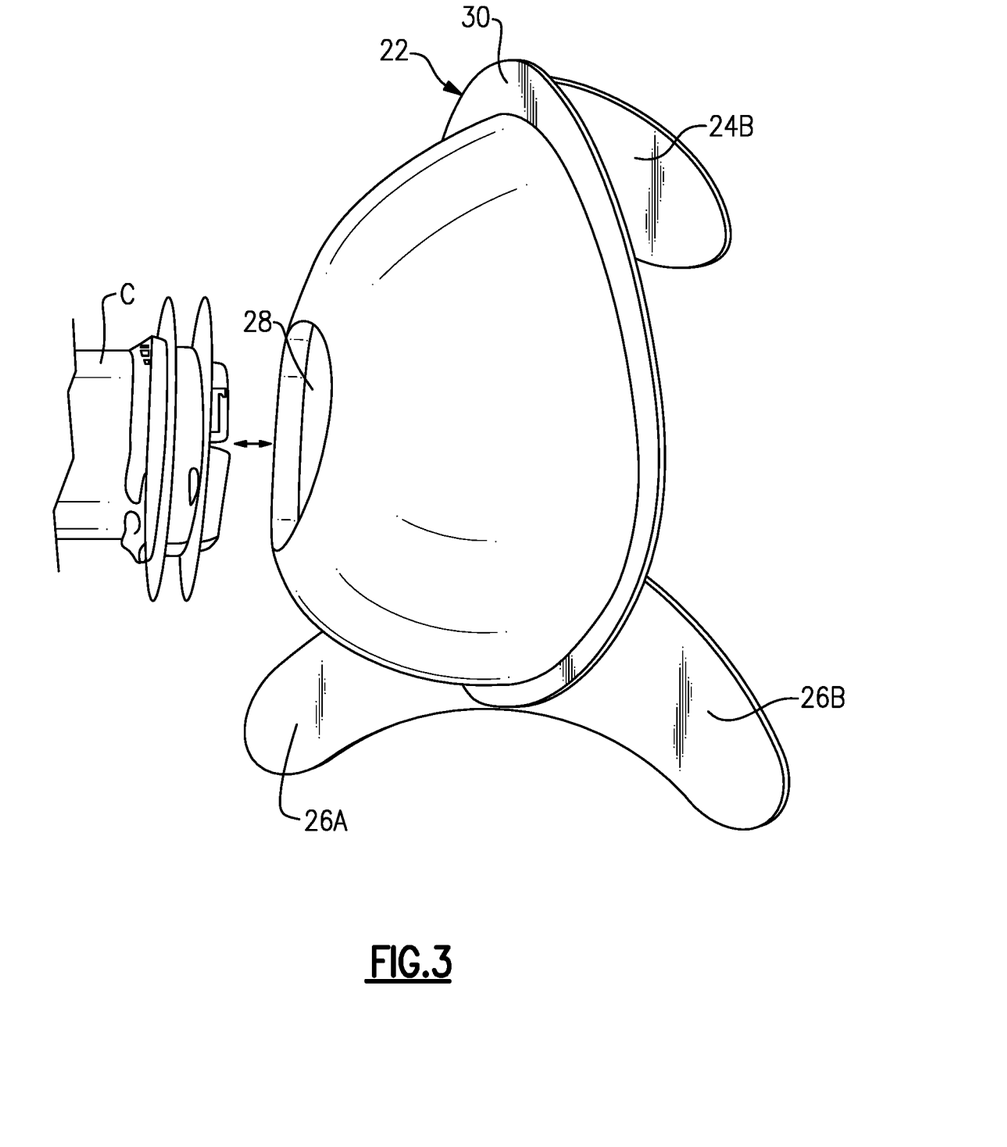
FIG. 3 is a side view of an example mask adjacent a conduit.

The central portion 22 of the mask 20 further includes an aperture 28 configured to receive a conduit C (FIG. 3) for delivering airflow. In one example, a rim 30 (perhaps best seen in FIG. 3) circumscribes the central portion 22. The rim 30 and wings 24A, 24B, 26A, 26B, are at least partially formed of an adhesive material in one embodiment. In another embodiment, the rim 30 is not made of adhesive material, with only the wings 24A, 24B, 26A, 26B being at least partially formed of adhesive material. In still another embodiment, the wings 24A, 24B, 26A, 26B are entirely formed of adhesive material.

Pre-term infants have less facial surface area than other patients. Despite the reduced surface area, a certain amount of adhesive contact area is still required to maintain an appropriate air seal between the mask 20 and the patient's face. Further, it is challenging to fit headgear on a pre-term infant. Accordingly, in this disclosure, wings 24A, 24B, 26A, 26B are sized and shaped to increase the total seal adhesion area around the patient's nose without being uncomfortable. The adhesive wings provide an appropriate seal without requiring any headgear.

In one example of this disclosure, in order to facilitate appropriate seal adhesion for pre-term infants, the upper and lower wings have a particular arrangement, which is optimized for comfort and adhesion. With reference to FIG. 2, the mask 20 has a centerline 32, and the mask 20 is substantially symmetrical about the centerline 32. As such, the arrangement of the wings 24A, 24B, 26A, 26B will be discussed relative to the upper wing 24A and the lower wing 26A. One should understand that the wings 24B and 26B are arranged substantially similar to the corresponding wing in the pair.

With reference to the upper wings, the upper wing 24A has an upper edge 34, a lower edge 36, and a rounded free end 38. The upper wing 24A projects from the rim 30 adjacent a top of the central portion 22. The upper and lower edges 34, 36 converge at the free end 38. The upper wing 24A projects generally along an axis $A_1$, which is oblique to the centerline 32. The upper edge 34 has a length $L_1$, and the lower edge 36 has a length $L_2$. The length $L_1$ is greater than the length $L_2$ in this example. The lengths $L_1$, $L_2$ are measured from an outer periphery of the rim 30 to the free end 38.

With reference to the lower wings, the lower wing 26A has an upper edge 40, a lower edge 42, and a rounded free end 44. The lower wing 26A projects from the rim 30 to the free end 44 generally along an axis $A_2$, which is oblique to the centerline 32. The upper edge 40 is curved and has a length $L_3$, which is less than a length $L_4$ of the lower edge 42. The length $L_4$ of the lower edge 42 is measured between the centerline 32 and the free end 44, in this example. In other examples, in which the lower edge 42 may project from the rim 30, the length $L_4$ would be measured in the same way as lengths $L_1$-$L_3$. Like the upper edge 40, the lower edge 42 is also curved. The lower edge 42 substantially follows a radius R having an origin O below the mask 20 and on the centerline 32. The upper edge 40 is curved such that it is substantially parallel to the lower edge 42, except adjacent the free end 44, at which point the upper and lower edges 40, 42 converge.

In order to optimize the shape of the wings 24A, 24B, 26A, 26B for maximum comfort and adhesion, the various proportions of the upper wings 24A, 24B, and lower wings 26A, 26B, are controlled relative to one another, and are further controlled with respect to a maximum height $H_C$ and maximum width $W_C$ of the central portion 22.

In one example, the ratio of $H_L/H_U$ is between about 0.5 and 1.5, where $H_U$ is the height of the upper wings 24A, 24B, and $H_L$ is the height of the lower wings 26A, 26B. The heights $H_U$, $H_L$ are measured from an absolute top of the wing to an absolute bottom. In a more particular embodiment, the ratio of $H_L/H_U$ is between about 0.6 and 1.0. In an even more particular example, the ratio is about 0.78.

In one example, the ratio of $W_U/W_L$ is between about 0.6 and 1.0, where $W_U$ is the width of the mask 20 between the free ends 38 of the upper wings 24A, 24B, and $W_L$ is the width of the mask 20 between the free ends 44 of the lower wings 26A, 26B. In a more particular example, the ratio of $W_U/W_L$ is between about 0.7 and 0.9. In an even more particular example, the ratio is about 0.81.

In one example, the ratio $H_U/H_C$ is between about 0.1 and 0.5. In a more particular example, the ratio is between about 0.2 and 0.4. In an even more particular example, the ratio is about 0.34.

In one example, the ratio $H_L/H_C$ is between about 0.1 and 0.5. In a more particular example, the ratio is between about 0.2 and 0.4. In an even more particular example, the ratio is about 0.27.

In one example, the ratio $W_C/W_L$ is between about 0.4 and 0.8. In a more particular example, the ratio is between about 0.5 and 0.7. In an even more particular example, the ratio is about 0.59.

In one example, the ratio $W_C/W_U$ is between about 0.5 and 1.0. In a more particular example, the ratio is between about 0.6 and 0.9. In an even more particular example, the ratio is about 0.76.

The above-discussed ratios, both together and separately, have criticality to the mask 20. Again, the mask 20 provides an optimized level of comfort and adhesion. Masks according to this disclosure can include one or more of the above-discussed ratios. The mask 20 in the figures includes each of the above-discussed ratios in combination, but this disclosure is not limited to masks that include the above-discussed ratios.

In one example, mask 20 is shaped to somewhat resemble a cartoon animal, with the upper wings 24A, 24B and lower wings 26A, 26B being shaped to somewhat resemble the arms and legs of an animal, such as a bear. This increases the overall aesthetic of the mask 20, and can help to bring some levity to a potentially intense medical situation. In one embodiment, the mask 20 somewhat resembles a teddy bear, which is a universal symbol of comfort to newborn patients and their families. The mask 20 may be baby blue or pink, as examples. The mask 20 may also be a neutral color, such as grey.

While wings upper wings 24A, 24B extend over the upper cheek area and lower wings 26A, 26B extend in the area above the lip in the illustrated embodiment, it should be understood that the wings 24A, 24B, 26A, 26B may also extend over other portions of the face. Further, while various ratios have been discussed above, those ratios may be used to produce masks in a variety of different sizes. For instance, the mask 20 may be sized for use with all sizes of neonatal and pediatric patients. While the mask 20 is intended to eliminate the need for headgear, a simple elastic strap may be provided to apply minimal pressure on the mask 20 and reduce seal separation when a patient turns on their side.

In one example of this disclosure, the mask 20 is made entirely of silicone, or another type of soft elastomer. Certain portions of the mask 20 are formed at least partially of adhesive material, such that those portions of the mask 20 can be adhered to a patient's skin. Example portions of the mask include the wings 24A, 24B, 26A, 26B and rim 30. In one example, the adhesive material consists of a two compound silicone elastomer that cross-links at room temperature. A cross-link is a bond that links one polymer chain to another, and generally promotes a difference in the polymers' physical properties. Accordingly, the cross-linking reaction may be used to produce a gel with appropriate tact and other desirable attributes.

In one example method of making the mask 20, the fabrication of the mask 20 occurs in a two shot or two-part molding process. In a first step, at least a majority of the central portion 22 is molded of a first silicone material. In a second step, the above-discussed adhesive material is molded over material injected during the first step. In one example, the adhesive material partially forms the wings 24A, 24B, 26A, 26B and the rim 30. In another example, the adhesive material partially forms only the wings 24A, 24B, 26A, 26B, and the rim 30 is entirely formed in the first step. In this process, molding of mask 20 involves a multi-material injection molding (MMM) process that allows the initial silicone structure to mix and mold before a second mix of liquid silicone adhesive material is molded to the surface of the structure.

In another example of making the mask 20, the adhesive material is manually provided in a separate step after the molding of the initial mask structure. In this example, an adhesive gel is encased on two sides with a peel-off material and is die cut to shape the mask 20. The peel-off material is removed on one side of the gel, and that side is applied to the mask. The other peel-off portion is left on until the mask is applied to a patient.

The adhesive material may be formed from linear or branched silicones having reactive groups that undergo a crosslinking reaction during curing. Examples of crosslinking reactions include the hydrosilylation reaction in which a silicone having an Si—H reactive group reacts with a silicone having an aliphatically unsaturated reactive group in the presence of a platinum or rhodium catalyst. Alternatively, the reaction can involve the reaction of a silicone having an Si—OH reactive group with a silicone or a chain extender (e.g., a silane) having an alkoxy reactive group in the presence of a metal catalyst. In yet another alternative embodiment, a silicone having an Si—OH containing polymer is mixed with an alkoxysilane in the presence of a titanate catalyst.

Other components can be included in the gel adhesive of the present invention, including but not limited to, fillers, pigments, low temperature cure inhibitors, additives for improving adhesion, pharmaceutical agents, cosmetic agents, resins, fluids or other materials conventionally used in gels.

The adhesive material is reusable and repositionable on the patients face while retaining its sticking strength. The adhesive material, in one example, has enough tack to support the weight of the mask 20 and any attached conduit, such as the conduit C. In this example, the adhesive material is provided integrally with the remainder of the mask 20, and is not provided by a strip or pad of adhesive.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A mask configured to deliver pressurized airflow, comprising:
   a central portion configured to surround a nose of a patient, wherein the central portion includes a rim circumscribing a section of the central portion projecting away from the rim, wherein the section is configured to receive the nose of the patient;
a first pair of wings projecting from opposite sides of the central portion, wherein the first pair of wings includes first and second wings; and
a second pair of wings projecting from opposite sides of the central portion, wherein each wing of the first and second pairs of wings is at least partially provided by an adhesive material, and wherein the adhesive material is integrally formed with the mask and the adhesive material is not provided by a strip or pad of adhesive, wherein the second pair of wings includes third and fourth wings,
wherein, when the mask is viewed from a front perspective, the first pair of wings are above the second pair of wings,
wherein the first pair of wings each include an upper edge having a length greater than a length of a lower edge,
wherein the second pair of wings each include an upper edge having a length less than a length of a lower edge,
wherein the first wing projects along a first axis oblique to a centerline of the mask such that an acute angle is formed, on a same side of the centerline as the first wing, between the first axis and the centerline by moving from the first axis in a direction generally downward and toward the centerline,
wherein the second wing projects along a second axis oblique to the centerline such that an acute angle is formed, on a same side of the centerline as the second wing, between the second axis and the centerline by moving from the second axis in a direction generally downward and toward the centerline,
wherein the third wing projects along a third axis oblique to the centerline such that an acute angle is formed, on a same side of the centerline as the third wing, between the third axis and the centerline by moving from the third axis in a direction generally downward and toward the centerline,
wherein the fourth wing projects along a fourth axis oblique to the centerline such that an acute angle is formed, on a same side of the centerline as the fourth wing, between the fourth axis and the centerline by moving from the fourth axis in a direction generally downward and toward the centerline,
wherein a skin-contacting region of the mask includes the rim and the first, second, third, and fourth wings,
wherein the skin-contacting region is formed at least partially of the adhesive material and is configured to be adhered to a skin of the patient,
wherein the section projects away from the skin-contacting region,
wherein the section includes an aperture configured to couple to a conduit, and
wherein the section is configured to surround the nose of the patient without being directly adhered to the skin of the patient.

2. The mask as recited in claim 1, wherein a ratio of a width of the central portion to the width of the mask between ends of the first pair of wings is between about 0.5 and 0.7.

3. The mask as recited in claim 2, wherein a ratio of the width of the central portion to the width of the mask between ends of the second pair of wings is between about 0.6 and 0.9.

4. The mask as recited in claim 3, wherein a ratio of a height of the second pair of wings to a height of the first pair of wings is between about 0.5 to 1.5.

5. The mask as recited in claim 4, wherein the ratio of the height of the second pair of wings to the height of the first pair of wings is between about 0.6 and 1.0.

6. The mask as recited in claim 5, wherein a ratio of the height of the first pair of wings to a height of the central portion is between about 0.1 and 0.5.

7. The mask as recited in claim 6, wherein a ratio of the height of the second pair of wings to a height of the central portion is between about 0.1 and 0.5.

8. The mask as recited in claim 1, wherein the mask is formed entirely of silicone.

9. The mask of claim 1, wherein the adhesive material is a two compound silicone elastomer.

10. The mask as recited in claim 1, wherein a ratio of the width of the mask between ends of the first pair of wings to the width of the mask between ends of the second pair of wings is between about 0.7 and 0.9.

11. The mask as recited in claim 1, wherein:
a top of the central portion is configured to rest on a bridge of the nose of the patient, and
a bottom of the central portion is configured to rest above an upper lip of the patient.

12. The mask as recited in claim 1, wherein the conduit is configured to deliver airflow.

13. The mask as recited in claim 1, wherein the adhesive material is integrally formed with the mask such that, after the mask is formed, the adhesive material is not configured to be separable from the mask.

14. The mask as recited in claim 1, wherein the adhesive material is directly connected to a remainder of the mask without an intervening adhesive.

15. The mask as recited in claim 1, wherein the adhesive material is integrally molded with the mask.

16. The mask as recited in claim 1, wherein the first and second pairs of wings are integrally molded with the central portion.

17. The mask as recited in claim 1, wherein the first and second pairs of wings are directly connected to the central portion without an intervening adhesive.

18. The mask as recited in claim 1, wherein the second pair of wings each include a lower edge curved following a radius having an origin below a bottom edge of the mask.

19. The mask as recited in claim 1, wherein each of the first pair of wings exhibits a first height and each of the second pair of wings exhibits a second height less than the first height.

20. The mask as recited in claim 1, wherein each lower edge is spaced-apart from a corresponding upper edge in the downward direction.

21. The mask as recited in claim 1, wherein the downward direction is parallel to the centerline.

22. A system for delivering pressurized airflow comprising:
a flow generator configured to output a pressurized airflow;
a conduit in fluid communication with the flow generator;
a mask in fluid communication with the conduit, the mask comprising:
a central portion configured to surround a nose of a patient, wherein the central portion includes a rim circumscribing a section of the central portion projecting away from the rim, wherein the section is configured to receive the nose of the patient;
a first pair of wings projecting from opposite sides of the central portion, wherein the first pair of wings includes first and second wings; and a second pair of wings projecting from opposite sides of the central portion, wherein each wing of the first and second pairs of wings is at least partially provided by an adhesive material, and wherein the adhesive material is integrally formed with the mask and the adhesive material is not provided by a strip or pad of adhesive, wherein a ratio of the width of the mask between ends of the first pair of wings to the width of the mask between ends of the second pair of wings is between about 0.7 and 0.9, wherein the second pair of wings includes third and fourth wings, wherein a ratio of a width of the central portion to the width of the mask between ends of the first pair of wings is between about 0.5 and 0.7, wherein a ratio of the width of the central portion to the width of the mask between ends of the second pair of wings is between about 0.6 and 0.9, wherein a ratio of a height of the second pair of wings to a height of the first pair of wings is between about 0.5 to 1.5, wherein the ratio of the height of the second pair of wings to the height of the first pair of wings is between about 0.6 and 1.0, wherein a ratio of the height of the first pair of wings to a height of the central portion is between about 0.1 and 0.5, wherein a ratio of the height of the second pair of wings to a height of the central portion is between about 0.1 and 0.5, wherein, when the mask is viewed from a front perspective, the first pair of wings are above the second pair of wings, wherein the first pair of wings each include an upper edge having a length greater than a length of a lower edge, wherein the second pair of wings each include an upper edge having a length less than a length of a lower edge, wherein the first wing projects along a first axis oblique to a centerline of the mask such that an acute angle is formed, on a same side of the centerline as the first wing, between the first axis and the centerline by moving from the first axis in a direction generally downward and toward the centerline, wherein the second wing projects along a second axis oblique to the centerline such that an acute angle is formed, on a same side of the centerline as the second wing, between the second axis and the centerline by moving from the second axis in a direction generally downward and toward the centerline, wherein the third wing projects along a third axis oblique to the centerline such that an acute angle is formed, on a same side of the centerline as the third wing, between the third axis and the centerline by moving from the third axis in a direction generally downward and toward the centerline, wherein the fourth wing projects along a fourth axis oblique to the centerline such that an acute angle is formed, on a same side of the centerline as the fourth wing, between the fourth axis and the centerline by moving from the fourth axis in a direction generally downward and toward the centerline, wherein the second pair of wings each include a lower edge curved following a radius having an origin below a bottom edge of the mask, wherein a skin-contacting region of the mask includes the rim and the first, second, third, and fourth wings, wherein the skin-contacting region is formed at least partially of the adhesive material and is configured to be adhered to a skin of the patient, wherein the section projects away from the skin-contacting region, wherein the section includes an aperture configured to couple to the conduit, and wherein the section is configured to surround the nose of the patient without being directly adhered to the skin of the patient.

23. A method of manufacturing a mask, comprising:

injecting a soft elastomer compound into a mold to form an initial structure of the mask, wherein the initial structure of the mask includes a central portion, wherein the central portion includes a rim circumscribing a section of the central portion projecting away from the rim, wherein the section is configured to receive a nose of the patient; and providing an adhesive gel on the surface of the initial structure, wherein the adhesive gel is injected into the mold and is molded to the surface of the initial structure such that the adhesive gel becomes integrally formed with the initial structure and the adhesive gel is not provided by a strip or pad of adhesive, wherein the adhesive gel at least partially forms a first pair of wings projecting from the central portion and a second pair of wings projecting from the central portion, each wing of the first and second pairs of wings is at least partially made of the adhesive gel, wherein the first pair of wings includes first and second wings, and the second pair of wings includes third and fourth wings, wherein, when the mask is viewed from a front perspective, the first pair of wings are above the second pair of wings, wherein the first pair of wings each include an upper edge having a length greater than a length of a lower edge, wherein the second pair of wings each include an upper edge having a length less than a length of a lower edge, wherein the first wing projects along a first axis oblique to a centerline of the mask such that an acute angle is formed, on a same side of the centerline as the first wing, between the first axis and the centerline by moving from the first axis in a direction generally downward and toward the centerline, wherein the second wing projects along a second axis oblique to the centerline such that an acute angle is formed, on a same side of the centerline as the second wing, between the second axis and the centerline by moving from the second axis in a direction generally downward and toward the centerline, wherein the third wing projects along a third axis oblique to the centerline such that an acute angle is formed, on a same side of the centerline as the third wing, between the third axis and the centerline by moving from the third axis in a direction generally downward and toward the centerline, wherein the fourth wing projects along a fourth axis oblique to the centerline such that an acute angle is formed, on a same side of the centerline as the fourth wing, between the fourth axis and the centerline by moving from the fourth axis in a direction generally downward and toward the centerline, wherein the second pair of wings each include a lower edge curved following a radius having an origin below a bottom edge of the mask, wherein a skin-contacting region of the mask includes the rim and the first, second, third, and fourth wings,
wherein the skin-contacting region is formed at least partially of the adhesive gel and is configured to be adhered to a skin of the patient,
wherein the section projects away from the skin-contacting region,
wherein the section includes an aperture configured to couple to a conduit, and
wherein the section is configured to surround the nose of the patient without being directly adhered to the skin of the patient.

\* \* \* \* \*